US009060266B2

(12) United States Patent
Kim et al.

(10) Patent No.: US 9,060,266 B2
(45) Date of Patent: Jun. 16, 2015

(54) APPARATUS AND METHOD OF PROVIDING MEDICAL DATA BASED ON A HANDOVER OF A MEDICAL SENSOR

(71) Applicant: Samsung Electronics Co., Ltd., Gyeonggi-do (KR)

(72) Inventors: Jun-Hyung Kim, Gyeonggi-do (KR); Jong-Hyo Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 81 days.

(21) Appl. No.: 13/779,261

(22) Filed: Feb. 27, 2013

(65) Prior Publication Data

US 2013/0223405 A1    Aug. 29, 2013

(30) Foreign Application Priority Data

Feb. 28, 2012  (KR) .................. 10-2012-0020319

(51) Int. Cl.
*H04W 12/02* (2009.01)
*G06F 19/00* (2011.01)
*A61B 5/00* (2006.01)
*H04L 29/08* (2006.01)
*H04W 36/30* (2009.01)
*H04W 76/00* (2009.01)

(52) U.S. Cl.
CPC ............ *H04W 12/02* (2013.01); *A61B 5/747* (2013.01); *A61B 5/0002* (2013.01); *H04L 67/12* (2013.01); *G06F 19/3418* (2013.01); *H04W 36/30* (2013.01); *H04W 76/007* (2013.01)

(58) Field of Classification Search
None
See application file for complete search history.

(56) References Cited

U.S. PATENT DOCUMENTS

| 8,121,673 | B2 | 2/2012 | Tran |
| 2006/0161295 | A1* | 7/2006 | Yun ............................ 700/236 |
| 2011/0025493 | A1* | 2/2011 | Papadopoulos et al. .. 340/539.12 |
| 2012/0050046 | A1* | 3/2012 | Satorius ..................... 340/573.1 |
| 2012/0053472 | A1* | 3/2012 | Tran ............................. 600/509 |
| 2012/0330109 | A1* | 12/2012 | Tran ............................. 600/301 |
| 2013/0009783 | A1* | 1/2013 | Tran ............................. 340/669 |
| 2014/0171753 | A1* | 6/2014 | Montejo et al. ............. 600/301 |
| 2014/0194702 | A1* | 7/2014 | Tran ............................. 600/301 |

FOREIGN PATENT DOCUMENTS

| JP | 2003-303239 | 10/2003 |
| KR | 1020080004124 | 1/2008 |
| KR | 100963698 | 6/2010 |
| WO | WO 2010/077851 | 7/2010 |

* cited by examiner

*Primary Examiner* — Kerri Rose
(74) *Attorney, Agent, or Firm* — The Farrell Firm, P.C.

(57) ABSTRACT

An apparatus and method are provided for providing medical data based on a handover of a medical sensor. The apparatus includes a medical data client that requests and receives the medical data from the medical sensor; a security module that manages access to the medical data; a data management unit that stores the received medical data; and an event handler that receives an abnormal condition notification from the medical sensor and sends a command to release access to the medical data, based on the abnormal condition notification.

22 Claims, 7 Drawing Sheets

US 9,060,266 B2

APPARATUS AND METHOD OF PROVIDING MEDICAL DATA BASED ON A HANDOVER OF A MEDICAL SENSOR

PRIORITY

This application claims priority under 35 U.S.C. §119(a) to Korean Patent Application Serial No. 10-2012-0020319, which was filed in the Korean Intellectual Property Office on Feb. 28, 2012, the entire disclosure of which is incorporated herein by reference.

BACKGROUND OF THE INVENTION

1. Field of the Invention

The present invention relates generally to an apparatus and method of providing medical data, and more particularly, to an apparatus and method of providing medical data based on a handover between a gateway for collecting home medical information and a gateway in an ambulance, when a sensor for measuring the home health information is moved to the ambulance.

2. Description of the Related Art

With the rapidly rising costs of medical care, medical services are moving from treatment-oriented services to prevention and diagnosis-oriented services.

In this regard, using Information Technology (IT) development and technological convergence, technologies are being developed to meet new consumer demands for prevention and diagnosis-oriented services and many companies are developing new medical services.

For prevention and diagnosis, medical services have been standardized for consumers or patients to get medical services at home, without having to go to hospital or see a medical expert. Such standardized medical services provide a sensor for measuring patient conditions and an Application Hosting Device (AHD) for collecting data measured by the sensor at home.

The medical services also provide a Wide Area Network (WAN) device, i.e., a type of a medical management service provider for receiving collected information from the AHD, and a Health Reporting Network (HRN) device, which performs a similar role as a hospital, an insurance company, etc., for receiving medical data from the medical management service provider.

In addition, a Local Area Network (LAN) interface and a Personal Area Network (PAN) interface are provided between the sensor and the AHD to deliver the data measured at home.

For example, when a patient is equipped with a medical sensor on his/her body, measured medical data can be stored in a storage device within the medical sensor. However, when the medical sensor includes a storage device within the medical sensor, the medical sensor's size and weight hinders its wearability.

Therefore, to reduce the size of the medical sensor, measured medical data may be delivered to and stored in a separate device, e.g., a wirelessly connected medical gateway.

However, during an emergency, a patient is often moved from their home to a hospital, e.g., via an ambulance. Therefore, a pairing procedure between the medical sensor attached to the patient and a medical gateway, e.g., in the ambulance, for the medical staff to check the patient's medical data should be performed.

However, if the patient is unconscious, it can be difficult to find out a password, e.g., a pin code, which is used to perform the pairing procedure between the medical sensor and the medical gateway within the ambulance.

Further, during an emergency situation, any delay in connecting the patient's medical sensor and the medical gateway may be dangerous for the patient.

SUMMARY OF THE INVENTION

The present invention is designed to address at least the problems and/or disadvantages described above and to provide at least the advantages described below.

Accordingly, an aspect of the present invention is to provide an apparatus and a method for delivering medical data by a handover of a medical sensor from a medical gateway at home to a medical gateway in an ambulance.

In accordance with an aspect of the present invention, an apparatus for providing medical data based on a handover of a medical sensor is provided. The apparatus includes a medical data client that requests and receives the medical data from the medical sensor; a security module that manages access to the medical data; a data management unit that stores the received medical data; and an event handler that receives an abnormal condition notification from the medical sensor and sends a command to release access to the medical data, based on the abnormal condition notification.

In accordance with another aspect of the present invention, a method of providing medical data based on a handover of a medical sensor is provided. The method includes requesting the medical data from the medical sensor; receiving the medical data from the medical sensor; storing the received medical data; receiving an abnormal condition notification from the medical sensor; and sending a command to release access to the medical data to the medical sensor, based on the abnormal condition notification.

In accordance with another aspect of the present invention, an apparatus for providing medical data based on a handover of a medical sensor is provided. The apparatus includes a medical sensor that measures the medical data; a medical data server that sends the medical data to a medical gateway, when a request for the medical data is received from the medical gateway; a security module that controls access to the medical data; and a condition handler that sends an abnormal condition notification to the medical gateway and makes an emergency call. When apparatus receives a request for the medical data from another medical gateway, based on the emergency call, the medical data server sends the medical data to the another medical gateway.

In accordance with another aspect of the present invention, a method of providing medical data based on a handover of a medical sensor is provided. The method includes measuring the medical data of the patient; receiving a request from a medical gateway for the medical data of the patient; sending the medical data to the medical gateway; detecting an abnormal condition of the patient from the medical data; sending an abnormal condition notification to the medical gateway, based on the abnormal condition; making an emergency call, based on the abnormal condition; receiving a request for the medical data from another medical gateway, based on the emergency call; and sending the medical data to the another medical gateway.

In accordance with another aspect of the present invention, an apparatus for providing medical data based on a handover of a medical sensor is provided. The apparatus includes a medical data client that requests and receives the medical data from the medical sensor; a security module that manages access to the medical data; a data management unit that stores the received medical data; and an event handler that receives an abnormal condition notification from the medical sensor, and sends information for accessing the apparatus to the medical sensor, based on the abnormal condition notification.

In accordance with another aspect of the present invention, a method is provided for a medical gateway to provide medical data based on a handover of a medical sensor. The method includes requesting the medical data from the medical sensor; receiving the medical data from the medical sensor; storing the received medical data; receiving, from the medical sensor, an abnormal condition notification; and sending access information for accessing the medical gateway to the medical sensor

BRIEF DESCRIPTION OF THE DRAWINGS

The above and other aspects, features, and advantages of certain embodiments of the present invention will become more apparent from the following detailed description taken in conjunction with the attached drawings, in which.

DETAILED DESCRIPTION OF EMBODIMENTS OF THE INVENTION

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

In accordance with an embodiment of the present invention, when a medical sensor that measures medical information of a user is handed over from a medical gateway for collecting the medical information measured at home to another gateway outside of the home, the medical sensor sends the user's medical information to the another gateway. Therefore, in an emergency, emergency staff may immediately check the patient's medical information and provide better medical treatment.

Figure 1:
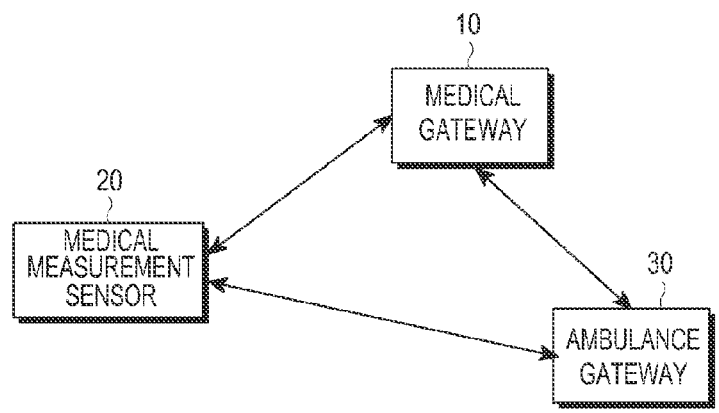
FIG. 1 illustrates a medical system for delivering medical information with a handover of a medical sensor, according to an embodiment of the present invention.

FIG. 1 illustrates a medical system for delivering medical information with a handover of a medical sensor, according to an embodiment of the present invention.

Referring to FIG. 1, the medical system includes a medical gateway 10, a medical measurement sensor 20, and an ambulance gateway 30.

The medical gateway 10 and the medical measurement sensor 20 are located at home, for example, and the medical measurement sensor 20 is worn by a user or attached to the user's body. For example, the medical gateway 10 and the medical measurement sensor 20 are connected based on a Universal Plug and Play (UPnP) home network service or other network service.

The medical gateway 10 performs service authentication with the medical measurement sensor 20, and receives and stores medical data, such as a patient's biological information, as measured by the service authenticated medical measurement sensor 20.

Upon reception of notification data that notifies of an abnormal condition from the medical measurement sensor 20, the medical gateway 10 sends a release access security command to release security of access to the medical measurement sensor 20. If medical data is requested by another device, the medical measurement sensor 20 may immediately send the requested medical data.

In accordance with another embodiment of the present invention, upon receipt of the notification data that notifies of the abnormal condition, the medical gateway 10 delivers its access information to the medical measurement sensor 20, so that the ambulance gateway 30 may collect patient information and medical history data stored in the medical gateway 10 by using the access information to access the medical gateway 10. Herein, the access information for the medical gateway 10 includes the medical gateway's 10 Internet Protocol (IP) address, an IDentifier (ID), and a password.

When the patient information and the medical history data are requested by the ambulance gateway 30, the medical gateway 10 sends the requested patient information and the medical history data to the ambulance gateway 30.

In accordance with another embodiment of the present invention, when the medical gateway 10 receives a request for the patient information and the medical history data, the medical gateway 10 sends access information to the medical measurement sensor 20 with the requested patient information and the medical history data to the ambulance gateway 30. The access information for accessing the medical measurement sensor 20 refers to information including access authority to allow the ambulance gateway 30 to access the medical measurement sensor 20. Accordingly, the ambulance gateway 30 uses the access information to access the medical measurement sensor 20 in order to immediately receive medical data measured by the medical measurement sensor 20.

The medical measurement sensor 20 performs service authentication with the medical gateway 10, measures medical data, such as the patient's health condition and biological information, and sends the measured medical data to the medical gateway 10. If an abnormal condition is found in the patient's medical information, the medical measurement sensor 20 sends notification data, which notifies of the abnormal condition of the patient, to the medical gateway 10, and receives a release access security command from the medical gateway 10.

In accordance with another embodiment of the present invention, the medical measurement sensor 20 receives the access information for the medical gateway 10 from the medical gateway 10. The medical measurement sensor 20 determines if the measured medical data exceeds a predetermined threshold, and if yes, determines an abnormal condition. Thereafter, the medical measurement sensor 20 makes an emergency call, e.g., calls an ambulance.

When the access information for the medical gateway 10 is requested by the ambulance gateway 30 within the ambulance, the medical measurement sensor 20 sends the requested access information for the medical gateway 10 to the ambulance gateway 30. The access information for the medical gateway 10 may be provided to the medical measurement sensor 20 from the medical gateway 10 with the service authentication between the medical gateway 10 and the medical measurement sensor 20, or the access information for the medical gateway 10 may be provided from the medical gateway 10, after the medical measurement sensor 20 sends a notification of an abnormal condition to the medical gateway 10.

When medical data is requested by the ambulance gateway 30, the medical measurement sensor 20 sends the requested medical data to the ambulance gateway 30.

The ambulance gateway 30, which is located inside the ambulance, discovers the medical measurement sensor 20 and identifies the medical measurement sensor 20 by performing a description process with the medical measurement sensor 20.

The ambulance gateway 30 requests and receives the access information for the medical gateway 10 from the medical measurement sensor 20, in order to obtain the patient's medical information.

Further, the ambulance gateway 30 requests and collects the patient information and the medical history data from the medical gateway 10, using the access information for accessing the medical gateway 10. When the medical measurement sensor 20 uses access security, the ambulance gateway 30 may also receive access information for accessing the medical measurement sensor 20 from the medical gateway 10.

When the medical measurement sensor 20 has released access security thereto, the ambulance gateway 30 requests and receives the medical data from the medical measurement sensor 20.

When the medical measurement sensor 20 uses the access security, the ambulance gateway 30 uses the received access information for accessing the medical measurement sensor 20 to request and receive the medical data from the medical measurement sensor 20.

As described above, when the medical sensor 20 is moved from the medical gateway 10 located at home, e.g., to an ambulance gateway 30, in accordance with an embodiment of the present invention, emergency staff will be able to deal quickly with a patient's conditions by directly providing the patient's medical data to a medical gateway in the another place e.g., the ambulance gateway 30.

Figure 2:
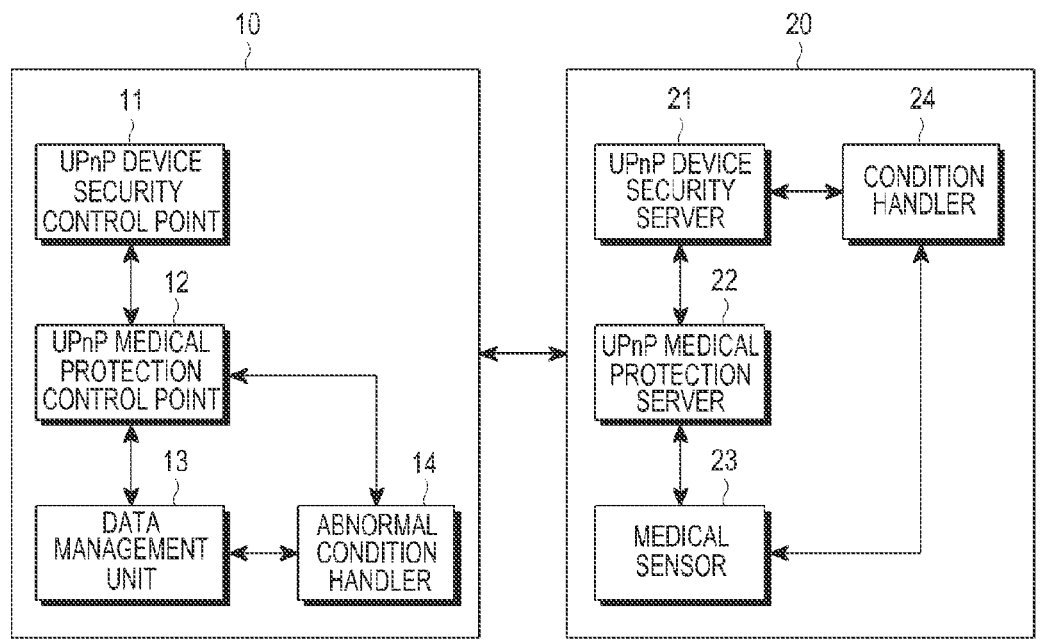
FIG. 2 illustrates a medical measurement sensor and a medical gateway, according to an embodiment of the present invention.

FIG. 2 illustrates a medical measurement sensor and a medical gateway, according to an embodiment of the present invention.

Referring to FIG. 2, the medical gateway 10 includes a UPnP device security control point 11, a UPnP medical protection control point 12, a data management unit 13, and an abnormal condition handler 14. Although FIG. 2 illustrates the UPnP device security control point 11, the UPnP medical protection control point 12, the data management unit 13, and the abnormal condition handler 14 as separate components in the medical gateway 10 for ease of description, these elements may combined into single controller or processor.

Herein, the terms "unit" and "module" each refer to a hardware device and a combination of a hardware device and software.

The medical measurement sensor 20 includes a UPnP device security server 21, a UPnP medical protection server 22, a medical sensor 23, and a condition handler 24, e.g., a processor.

The UPnP device protection control point 11 is a security module for managing access authority to data of the medical measurement sensor 20. The UPnP medical protection control point 12 is a medical data client for requesting and receiving medical data from the medical measurement sensor 20.

The data management unit 13 stores the received medical data or uses the received medical data to detect a patient's abnormal condition. The patient's abnormal condition may be detected by the medical measurement sensor 20 or by the medical gateway 10 using the received medical data.

The abnormal condition handler 14 is an event handler that sends an access security release command or the access information for accessing the medical gateway 10 to the medical measurement sensor 20, when an abnormal condition is detected by the medical measurement sensor 20 or the data management unit 13.

The UPnP device security server 21 is a security module for providing data access security. When receiving the access security release command from the medical gateway 10, the UPnP device security server 21 stops carrying out the access security. Further, when an access information request is received from the ambulance gateway 30 in the ambulance, the UPnP device security server 21 sends the requested access information for accessing the medical gateway 10 to the ambulance gateway 30.

The UPnP medical protection server 22 is a medical data server for delivering medical data measured by the medical measurement sensor 23 to the medical gateway 10. When the medical data is requested by the ambulance gateway 30, the UPnP medical protection server 22 sends the requested medical data to the ambulance gateway 30.

The medical sensor 23 measures the medical data, e.g., the patient's biological information.

The condition handler 24 detects an abnormal condition from the measured medical data, sends a notification of the abnormal condition to the medical gateway 10, and makes an emergency call, e.g., calls a family member, a hospital, etc., according to pre-stored information.

Figure 3:
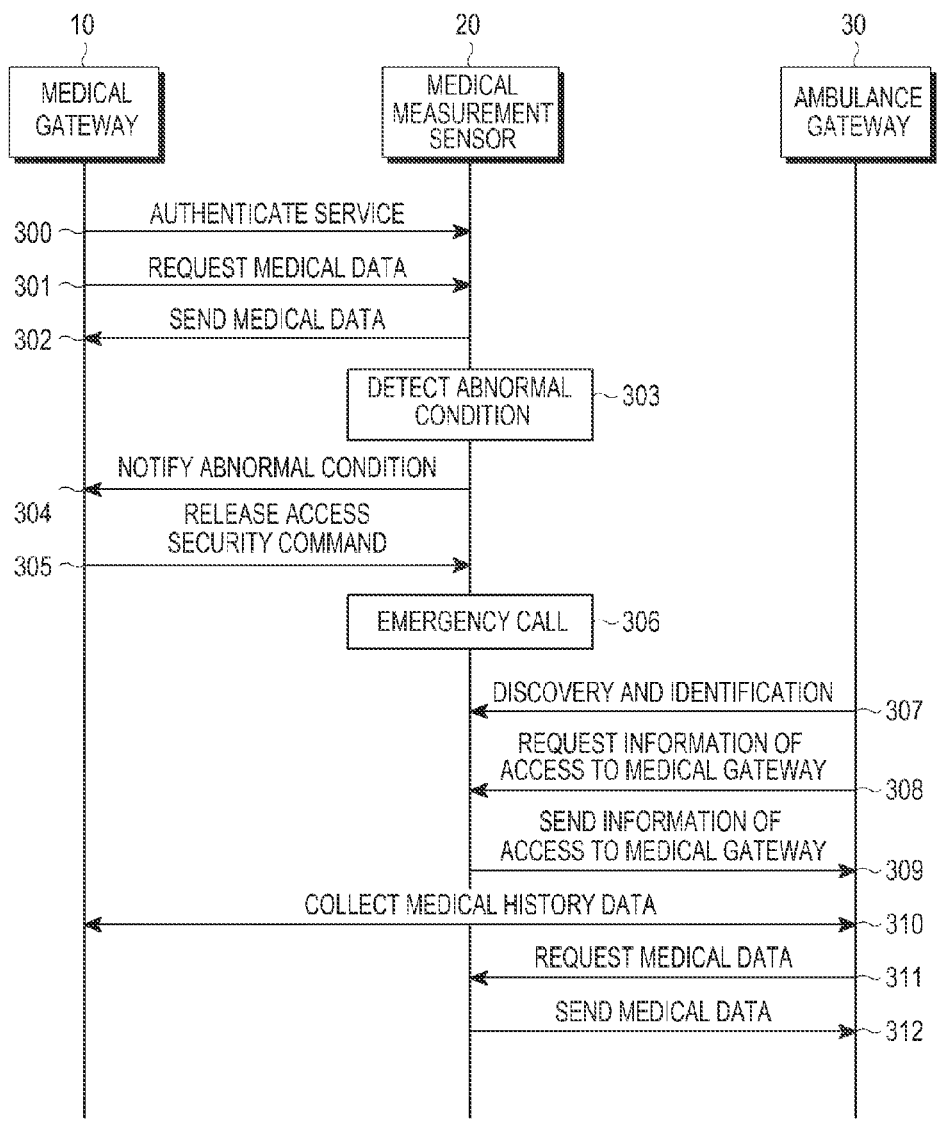
FIG. 3 is a signal flow diagram illustrating a procedure for providing medical data by releasing access security for a medical measurement sensor, according to an embodiment of the present invention.

FIG. 3 is a signal flow diagram illustrating a procedure for providing medical data by releasing access security for a medical measurement sensor, according to an embodiment of the present invention.

Referring to FIG. 3, in step 300, the medical gateway 10 performs service authentication with the medical measurement sensor 20, which is located at home, e.g., by using a UPnP home network service.

In step 301, the medical gateway 10 requests a patient's medical data from the medical measurement sensor 20, and in step 302, the medical measurement sensor 20 sends the requested medical data to the medical gateway 10.

In step 303, the medical measurement sensor 20 detects an abnormal condition, and in step 304, the medical measurement sensor 20 notifies the medical gateway 10 of the abnormal condition. For example, if measured medical data exceeds a predetermined threshold, the medical measurement sensor 20 determines there is an abnormality in the patient's health.

In step 305, the medical gateway 10 sends an access security release command to the medical measurement sensor 20. The access security release command commands the medical measurement sensor 20 to release the patient's medical data.

In step 306, the medical measurement sensor 20 makes an emergency call, e.g., to a predetermined family member or a hospital.

When the medical measurement sensor 20 is moved to an ambulance where the ambulance gateway 30 is located, the ambulance gateway 30 discovers and identifies the medical measurement sensor 20 in step 307.

In step 308, the ambulance gateway 30 requests a access information to access the medical gateway 10 from the medical measurement sensor 20.

In step 309, the medical measurement sensor 20 sends the requested access information for accessing the medical gateway 10 to the ambulance gateway 30.

In step 310, the ambulance gateway 30 uses the received access information to collect patient information and medical history data, such as a patient's disease history and a measured medical data history, from the medical gateway 10.

In step 311, the ambulance gateway 30 requests medical data from the medical measurement sensor 20, and in step 312, the medical measurement sensor 20 sends the medical data to the ambulance gateway 30.

Figure 4:
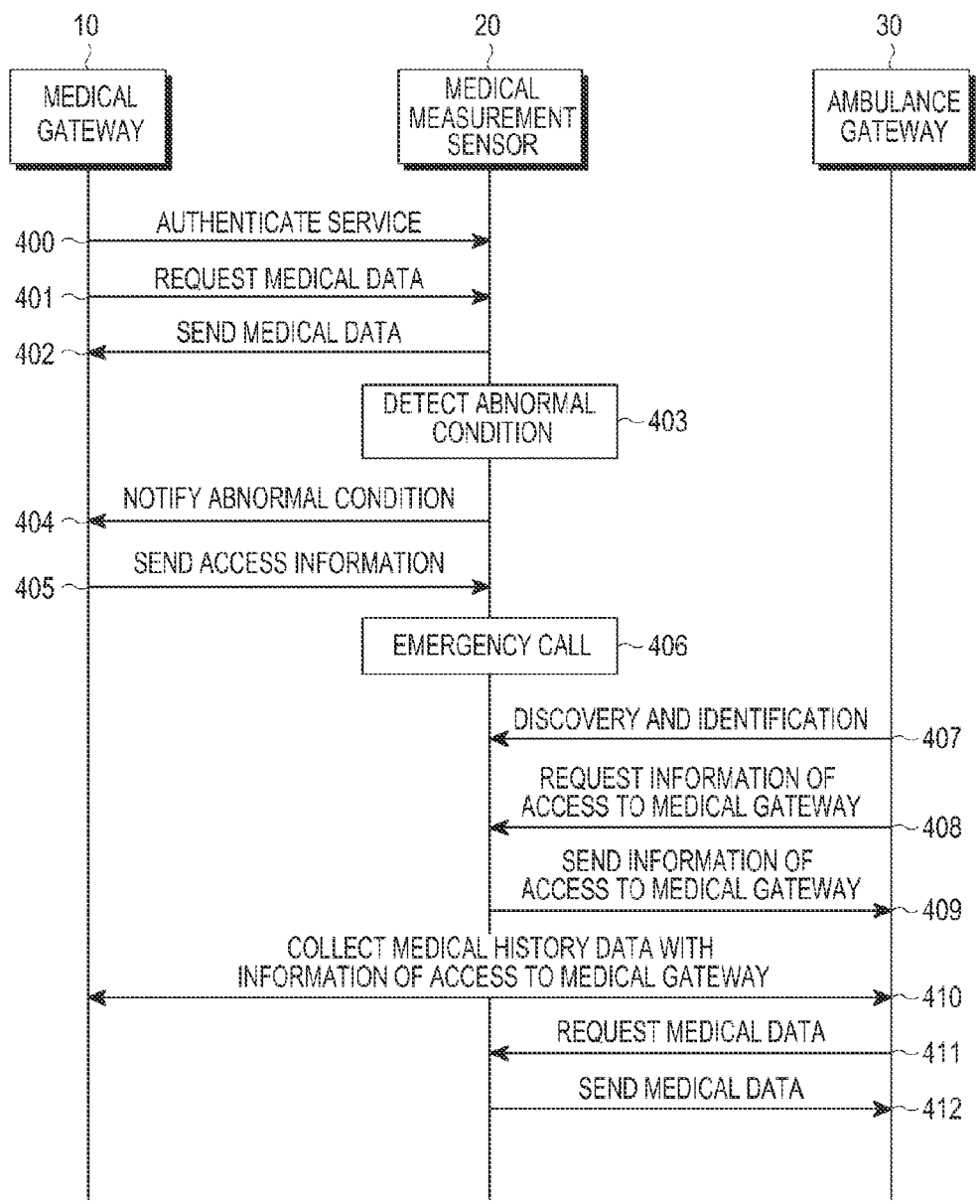
FIG. 4 is a signal flow diagram illustrating a procedure for providing medical data when access security of a medical measurement sensor is active, according to an embodiment of the present invention.

FIG. 4 is a signal flow diagram illustrating a procedure for providing medical data, when access security of a medical measurement sensor is active, according to an embodiment of the present invention.

In step 400, the medical gateway 10 performs service authentication with the medical measurement sensor 20 located at home, e.g., by using the UPnP home network service.

In step 401, the medical gateway 10 requests a patient's medical data from the medical measurement sensor 20, and in step 402, the medical measurement sensor 20 sends the requested medical data to the medical gateway 10.

In step 403, the medical measurement sensor 20 detects an abnormal condition, and in step 404, notifies the medical gateway 10 of the abnormal condition. For example, when the measured medical data exceeds a predetermined threshold, the medical measurement sensor 20 determines there is an abnormality in the patient's health.

In step 405, the medical gateway 10 sends access information for accessing the medical gateway 10 to the medical measurement sensor 20.

In step 406, the medical measurement sensor 20 makes an emergency call, e.g., to a predetermined family member or a hospital.

When the medical measurement sensor 20 is moved to an ambulance where the ambulance gateway 30 is located, the ambulance gateway 30 discovers and identifies the medical measurement sensor 20 in step 407.

In step 408, the ambulance gateway 30 requests, from the medical measurement sensor 20, the access information for accessing the medical gateway 10.

In step 409, the medical measurement sensor 20 sends the requested access information for the medical gateway 10 to the ambulance gateway 30.

In step 410, the ambulance gateway 30 uses the received access information to access to the medical gateway 10 and collect patient information and medical history data, e.g., a patient's disease history and a measured medical data history.

In step 411, the ambulance gateway 30 requests medical data from the medical measurement sensor 20, and in step 412, the medical measurement sensor 20 sends the requested medical data to the ambulance gateway 30.

Figure 5:
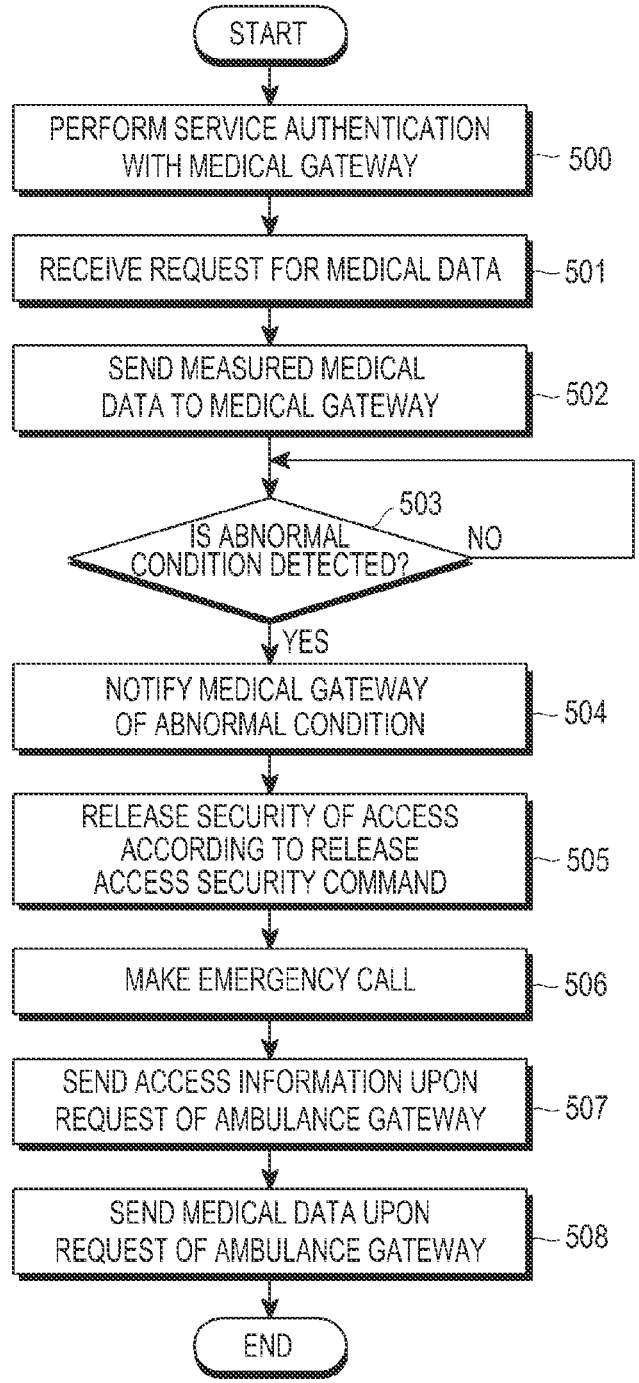
FIG. 5 is a flowchart illustrating a procedure of a medical measurement sensor delivering medical data, according to an embodiment of the present invention.

FIG. 5 is a flowchart illustrating a procedure of a medical measurement sensor for delivering medical data, according to an embodiment of the present invention.

Referring to FIG. 5, in step 500, the medical measurement sensor 20 performs service authentication with the medical gateway 10.

In step 501, the medical measurement sensor 20 receives a request for medical data from the medical gateway 10, and in step 502, the medical measurement sensor 20 sends measured medical data to the medical gateway 10.

In step 503, the medical measurement sensor 20 detects an abnormal condition in the patient's health.

In step 504, the medical measurement sensor 20 sends a notification of the abnormal condition to the medical gateway 10.

In step 505, the medical measurement sensor 20 receives a access security release command from the medical gateway 10 and releases access security to the medical data.

In step 506, the medical measurement sensor 20 makes an emergency call.

In step 507, the medical measurement sensor 20 receives an access information request to the medical gateway 10 from the ambulance gateway 30 within the ambulance, and sends the requested access information to the ambulance gateway 30.

In step 508, the medical measurement sensor 20 receives a request for medical data from the ambulance gateway 30 and then sends the requested medical data to the ambulance gateway 30.

Figure 6:
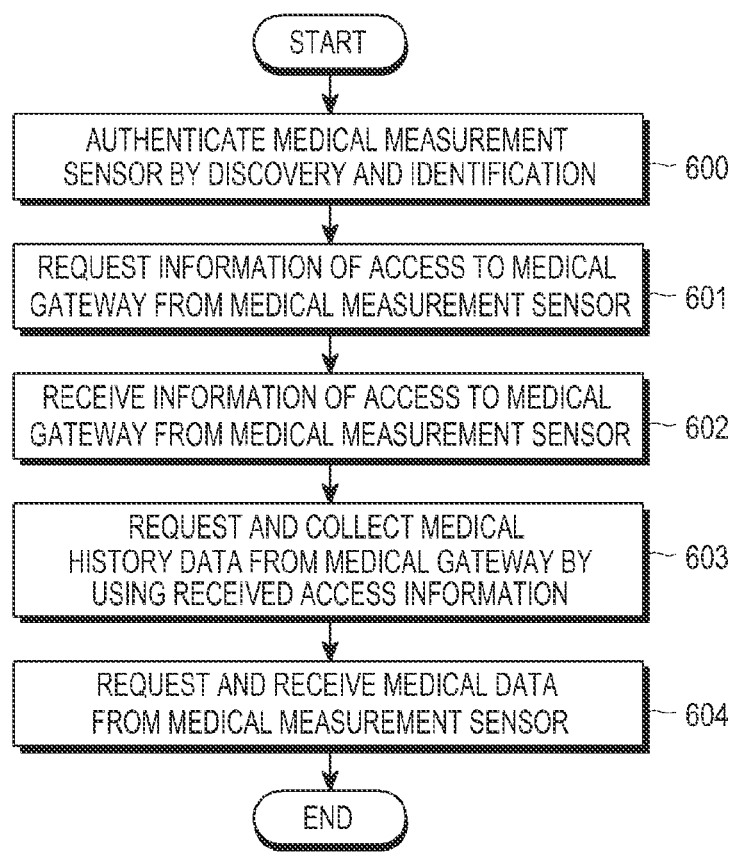
FIG. 6 is a flowchart illustrating a procedure of an ambulance gateway receiving medical information from a medical measurement sensor with released access security and a medical gateway, according to an embodiment of the present invention.

FIG. 6 is a flowchart illustrating a procedure of an ambulance gateway receiving medical information from a medical measurement sensor with released access security and a medical gateway 10, according to an embodiment of the present invention.

Referring to FIG. 6, in step 600, the ambulance gateway 30 discovers the medical measurement sensor 20 and performs authentication through identification of the discovered medical measurement sensor 20.

In step 601, the medical gateway 30 requests access information for accessing the medical gateway 10 from the medical measurement sensor 20.

In step 602, the ambulance gateway 30 receives the access information from the medical measurement sensor 20.

In step 603, the ambulance gateway 30 uses the received access information to access the medical gateway 10, request medical history data from the medical gateway 10, and receive and collect the requested medical history data from the medical gateway 10. For example, the ambulance gateway 30 may request and collect the medical history data and also patient information.

In step 604, the ambulance gateway 30 requests medical data from the medical measurement sensor 20 and receives the requested the medical data from the medical measurement sensor 20.

Figure 7:
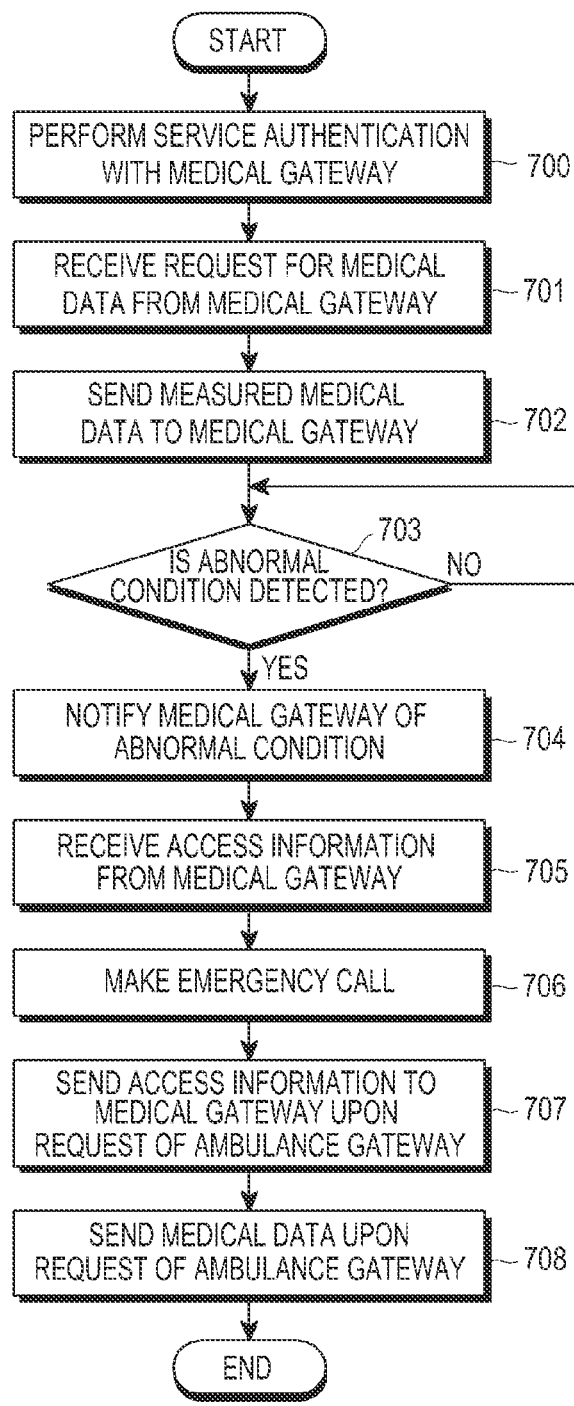
FIG. 7 is a flowchart illustrating a procedure of a medical measurement sensor delivering medical data, according to an embodiment of the present invention.

FIG. 7 is a flowchart illustrating a procedure of a medical measurement sensor for delivering medical data, according to an embodiment of the present invention.

Referring to FIG. 7, in step 700, the medical measurement sensor 20 performs service authentication with the medical gateway 10.

In step 701, the medical measurement sensor 20 receives a request for the medical data from the medical gateway 10, and in step 702, the medical measurement sensor 20 sends measured medical data to the medical gateway 10.

In step 703, the medical measurement sensor 20 determines an abnormal condition is detected in the patient's health.

In step 704, the medical measurement sensor 20 sends a notification of the abnormal condition to the medical gateway 10.

In step 705, the medical measurement sensor 20 receives access information for accessing the medical gateway 10 from the medical gateway 10.

In step 706, the medical measurement sensor 20 makes an emergency call.

In step 707, the medical measurement sensor 20 receives a request for the access information for accessing the medical gateway 10 from the ambulance gateway 30, and sends the requested access information to the ambulance gateway 30.

In step 708, the medical measurement sensor 20 receives a request for medical data including the access information from the ambulance gateway 10 and sends the requested medical data to the ambulance gateway 30.

Figure 8:
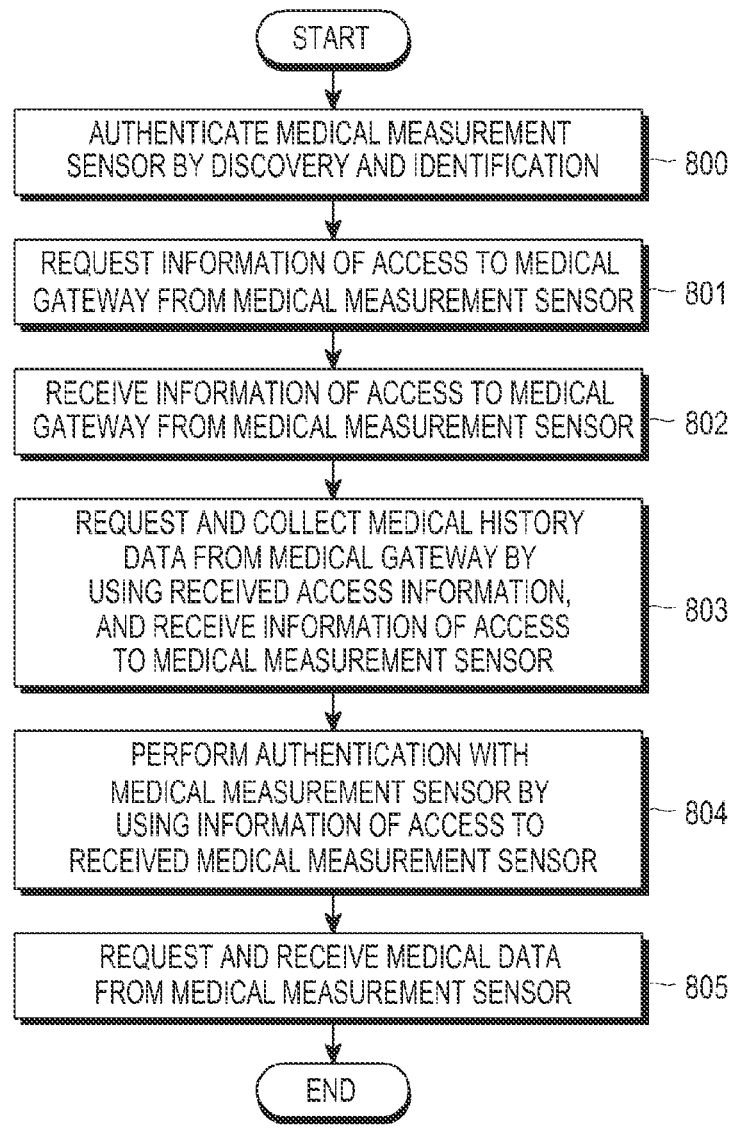
FIG. 8 is a flowchart illustrating a procedure of an ambulance gateway receiving medical information from a medical measurement sensor and a medical gateway with active access securities, according to an embodiment of the present invention.

FIG. 8 is a flowchart illustrating a procedure of an ambulance gateway for receiving medical information from a medical measurement sensor and a medical gateway with active access securities, according to an embodiment of the present invention.

Referring to FIG. 8, in step 800, the ambulance gateway 30 discovers the medical measurement sensor 20 and performs authentication through identification of the discovered medical measurement sensor 20.

In step 801, the medical gateway 30 requests access information for accessing the medical gateway 10 from the medical measurement sensor 20.

In step 802, the ambulance gateway 30 receives the information for accessing the medical gateway 10 from the medical measurement sensor 20.

In step 803, the ambulance gateway 30 uses the received access information to request medical history data from the medical gateway 10. In return, the ambulance gateway 30 receives and collects the requested medical history data from the medical gateway 10 and receives access information for accessing the medical measurement sensor 20. Using the access information for accessing the medical measurement sensor 20, the ambulance gateway 30 requests medical data from the medical measurement sensor 20. The ambulance gateway 30 may request and collect the medical history data and also the patient information.

In step 804, the ambulance gateway 30 uses the received access information to perform authentication with the medical measurement sensor 20, and in step 805, requests medical data from the medical measurement sensor 20 and then receives the requested medical data from the medical measurement sensor 20.

As described above, when the medical sensor is moved to another place from the medical gateway located at home, the above-described embodiments of the present invention directly provide a patient's medical data to a medical gateway in another place, thereby allowing emergency staff to quickly deal with a patient's condition in an emergency.

While the present invention has been particularly shown and described with reference to certain embodiments thereof, it will be understood by those of ordinary skill in the art that various changes in form and details may be made therein without departing from the spirit and scope of the present invention as defined by the following claims and their equivalents.

What is claimed is:

1. An apparatus for providing medical data based on a handover of a medical sensor, the apparatus comprising:
    a medical data client that requests the medical data to the medical sensor and receives the medical data from the medical sensor;
    a security module that manages access to the medical data;
    a data management unit that stores the received medical data; and
    an event handler that receives a predetermined condition notification from the medical sensor and sends a command to release access to the medical data, based on the predetermined condition notification.

2. The apparatus of claim 1, wherein the medical data comprises a biological condition of a patient measured by the medical sensor.

3. The apparatus of claim 1, wherein the data management unit stores disease history information of a patient, and medical history data received from the medical sensor.

4. The apparatus of claim 3, wherein the medical data client sends the disease history information and the medical history data to a medical gateway, when the disease history information and the medical history data are requested by the gateway.

5. A method of a medical gateway for providing medical data based on a handover of a medical sensor, the method comprising:
    requesting the medical data to the medical sensor;
    receiving the medical data from the medical sensor;
    storing the received medical data;
    receiving a predetermined condition notification from the medical sensor; and
    sending a command to release access to the medical data to the medical sensor, based on the predetermined condition notification.

6. The method of claim 5, wherein the medical data includes a biological condition of a patient measured by the medical sensor.

7. The method of claim 5, further comprising storing disease history information of a patient, and medical history data received from the medical sensor.

8. The method of claim 7, further comprising:
    receiving a request for the disease history information and the medical history data from another gateway; and
    sending the disease history information and the medical history data to the another medical gateway.

9. An apparatus for providing medical data based on a handover of a medical sensor, the apparatus comprising:
    a medical data client that requests the medical data to the medical sensor and receives the medical data from the medical sensor;
    a security module that manages access to the medical data;
    a data management unit that stores the received medical data; and
    an event handler that receives a predetermined condition notification from the medical sensor, and sends information for accessing the apparatus to the medical sensor, based on the predetermined condition notification.

10. The apparatus of claim 9, wherein the medical data comprises a biological condition of a patient measured by the medical sensor.

11. The apparatus of claim 10, wherein the data management unit stores disease history information of a patient, and medical history data received from the medical sensor.

12. The apparatus of claim 11, wherein the medical data client sends the disease history information and the medical history data with access authority information to access the medical sensor to a medical gateway, when the disease history information and the medical history data are requested by the gateway.

13. A method of a medical gateway for providing medical data based on a handover of a medical sensor, the method comprising:
   requesting the medical data to the medical sensor;
   receiving the medical data from the medical sensor;
   storing the received medical data;
   receiving, from the medical sensor, a predetermined condition notification; and
   sending access information for accessing the medical gateway to the medical sensor.

14. The method of claim 13, wherein the medical data includes a biological condition of a patient measured by the medical sensor.

15. The method of claim 13, further comprising storing disease history information of a patient, and medical history data received from the medical sensor.

16. The method of claim 15, further comprising:
   receiving a request for the disease history information and the medical history data from another gateway; and
   sending the disease history information and the medical history data to the another medical gateway.

17. An apparatus for providing medical data of a patient based on a handover of a medical sensor, the apparatus comprising:
   a medical sensor that measures the medical data;
   a medical data server that sends the medical data to a medical gateway, when a request for the medical data is received from the medical gateway;
   a security module that controls access to the medical data; and
   a condition handler that sends a predetermined condition notification to the medical gateway and makes an emergency call,
   wherein when the apparatus receives a request for the medical data from another medical gateway, based on the emergency call, the medical data server sends the medical data to the another medical gateway.

18. The apparatus of claim 17, wherein the medical data comprises a biological condition of the patient measured by the medical sensor.

19. The apparatus of claim 17, wherein the security module receives a request from the another medical gateway for access information for accessing the medical gateway, and sends the access information to the another medical gateway.

20. A method of a medical measurement sensor for providing medical data of a patient based on a handover thereof, the method comprising:
   measuring the medical data of the patient;
   receiving a request from a medical gateway for the medical data of the patient;
   sending the medical data to the medical gateway;
   detecting a predetermined condition of the patient from the medical data;
   sending a predetermined condition notification to the medical gateway, based on the predetermined condition;
   making an emergency call, based on the predetermined condition;
   receiving a request for the medical data from another medical gateway, based on the emergency call; and
   sending the medical data to the another medical gateway.

21. The method of claim 20, wherein the medical data includes a biological condition of the patient measured by the medical measurement sensor.

22. The method of claim 20, further comprising:
   receiving a request from the another medical gateway for access information for accessing the medical gateway; and
   sending the access information to the another medical gateway.

* * * * *